United States Patent [19]

Hamanaka et al.

[11] Patent Number: 4,622,410

[45] Date of Patent: Nov. 11, 1986

[54] BICYCLO[3,3,0]OCTAN-3-ONES

[75] Inventors: Nobuyuki Hamanaka, Kyoto; Hideo Takada; Yoshinobu Arai, both of Osaka, all of Japan

[73] Assignee: Ono Pharmaceutical Co. Ltd., Osaka, Japan

[21] Appl. No.: 712,446

[22] Filed: Mar. 18, 1985

[30] Foreign Application Priority Data

Mar. 19, 1984 [JP] Japan ................................. 59-51058

[51] Int. Cl.$^4$ ........................................... C07D 307/93
[52] U.S. Cl. ..................................... 549/304; 549/305; 549/214; 560/121; 562/503; 564/189; 568/379
[58] Field of Search ........................ 549/304, 305, 214

[56] References Cited

U.S. PATENT DOCUMENTS 4,558,142 10/1985 Holland et al. ...................... 549/305

OTHER PUBLICATIONS

Tetrahedron Letters, vol. 25, 21, pp. 2199-2200 (1984)—this article was published on 8th May, 1984, after the priority date of the present application which is 19th Mar. 1984—The Synthesis of 2,3-Dinor-6-Oxo-Prostaglandin F$_{2\alpha}$ from a Prostaglandin Lactone Intermediate, and the Reaction Scheme Produces 2,3-Dinor-6-Oxo-PGF$_{1\alpha}$, but no Other 6-Keto-PG.

Primary Examiner—Jane T. Fan
Attorney, Agent, or Firm—Stevens, Davis, Miller & Mosher

[57] ABSTRACT

The present invention relates to intermediates of the general formula:

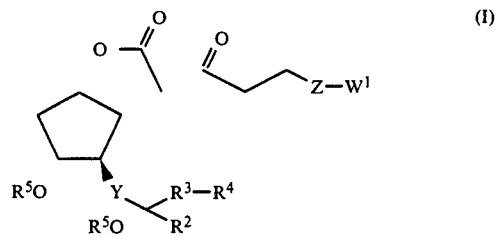

(wherein Y and Z, which may be the same or different, each represents a trans-vinylene group or an ethylene group, $R^2$ represents a hydrogen atom or a methyl or ethyl group, $R^3$ represents a single bond or an alkylene group of 1 to 5 carbon atoms, $R^4$ represents an alkyl group of 1 to 8 carbon atoms, a cycloalkyl group of 4 to 7 carbon atoms unsubstituted or substituted by at least one alkyl group of 1 to 8 carbon atoms or a phenyl or phenoxy group unsubstituted or substituted by at least one halogen atom, trifluoromethyl group or alkyl group of 1 to 4 carbon atoms, $R^5$ represents a hydroxy- protecting group which can be removed in acidic conditions and $W^1$ represents a group of the formula: —COOR$^1$, —CON(R$^6$)$_2$, —CH$_2$OR$^5$ or —CH(OR$^7$)CH$_2$OR$^5$ (in which R$^1$ represents a hydrogen atom or an alkyl group of 1 to 12 carbon atoms, the groups R$^6$, which may be the same or different, each represents an alkyl group of 1 to 4 carbon atoms, a phenyl group or an aralkyl group of 7 to 12 carbon atoms or R$^7$ represents an acyl group of 2 to 12 carbon atoms and R$^5$ is as hereinbefore defined) with the proviso that, when R$^3$ represents a single bond, R$^4$ does not represent a substituted or unsubstituted phenoxy group, which are useful in the preparation of 6-keto-prostaglandin derivatives.

8 Claims, No Drawings

BICYCLO[3,3,0]OCTAN-3-ONES

This invention relates to intermediates useful in the preparation of 6-keto-prostaglandin derivatives, to a process for their preparation, and to their use.

The 6-keto-prostaglandin derivatives 6-keto-PGE$_1$ and 6-keto-PGF$_{1\alpha}$ are compounds of the formula:

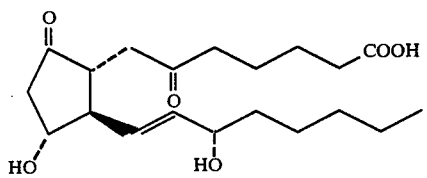

6-keto-PGE$_1$ and

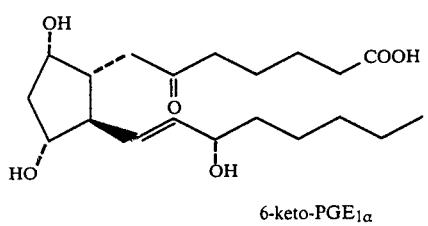

6-keto-PGE$_{1\alpha}$

They and their analogues possess the valuable pharmacological properties typical of the prostaglandins in a selective fashion, in particular hypotensive activity, inhibitory activity on gastric acid secretion and gastric ulceration, stimulatory activity on uterine contraction and abortifacient, luteolytic and antinidatory activity, and are useful in the treatment of hypertension, in the treatment of disorders of the peripheral circulation, in the prevention and treatment of cerebral thrombosis and myocardial infarction, in the treatment of gastric ulceration, in the termination of pregnancy and induction of labour in pregnant female mammals, in the treatment of impaired fertility and in the control of oestrus, contraception and menstrual regulation in female mammals. (see U.S. Pat. No. 4,215,142 and German Patent Specification No. 2753986).

The 6-keto-PGE$_1$ derivative 2-decarboxy-2-glycoloyl-6-keto-PGE$_1$ of the formula:

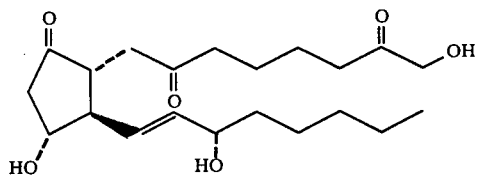

possesses selectively a strong cytoprotective activity and very low toxicity, having relatively weak pharmacological properies typical of other prostaglandins, and therefore can be used as a very effective agent for the treatment of cyto-damage (in the treatment of diseases of various organisms or systems in human beings associated with cytodamage) (see U.S. Pat. No. 4,443,478).

Accordingly 6-keto-prostaglandin analogues (such as 6-keto-PGE$_1$ and 6-keto-PGF$_{1\alpha}$ and their analogues which are referred to hereinafter as 6-keto-PGs) show more selective pharmacological activities associated with modified parts of the analogues' molecular skeletons and are expected to be developed as medicines in the future.

A known process for the preparation of 6-keto-PGs (see U.S. Pat. No. 4,215,142) is shown in Scheme A in which THP represents a tetrahydropyran-2-yl group. This known process has the disadvantage of requiring many process steps.

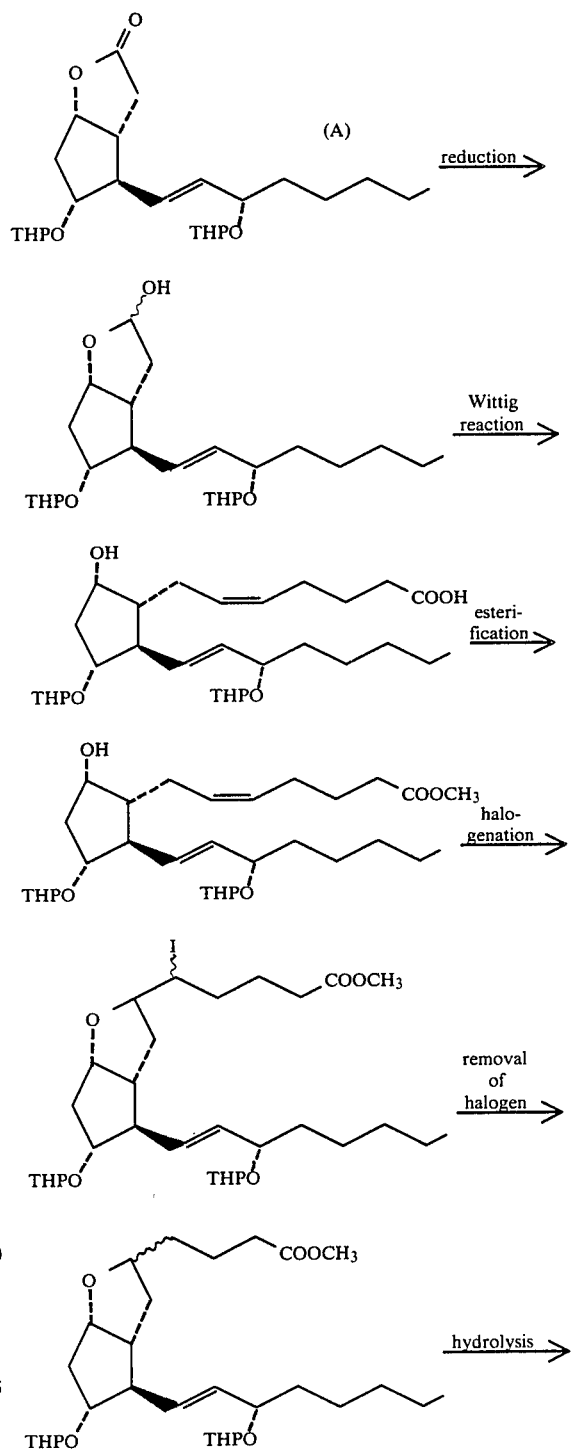

Scheme A

Scheme A -continued

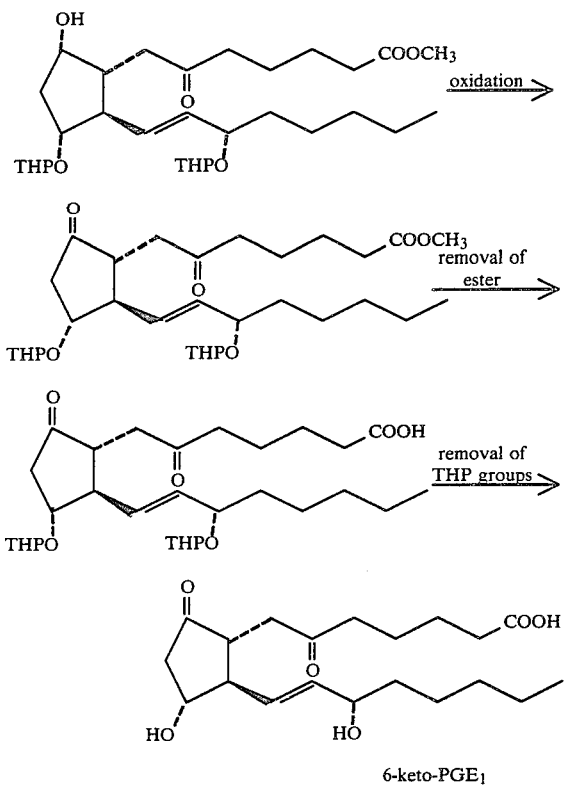

6-keto-PGE$_1$

In other known processes for the preparation of 6-keto-PGE$_1$, the α-side chain may be introduced at a different stage of the reaction sequence. However in such processes only the order of the reaction steps is changed. The known process depicted in Scheme A has been chosen to provide the clearest comparison with the new preparation process using intermediates according to the present invention.

It has now been discovered that, for example, 6-keto-PGE$_1$ may be prepared by a new sequence of reactions, via novel intermediate compounds, as shown in Scheme B, wherein THP is as hereinbefore defined.

Scheme B

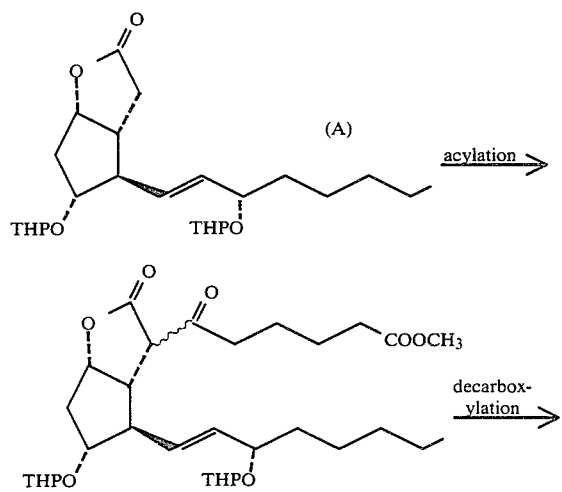

Scheme B -continued

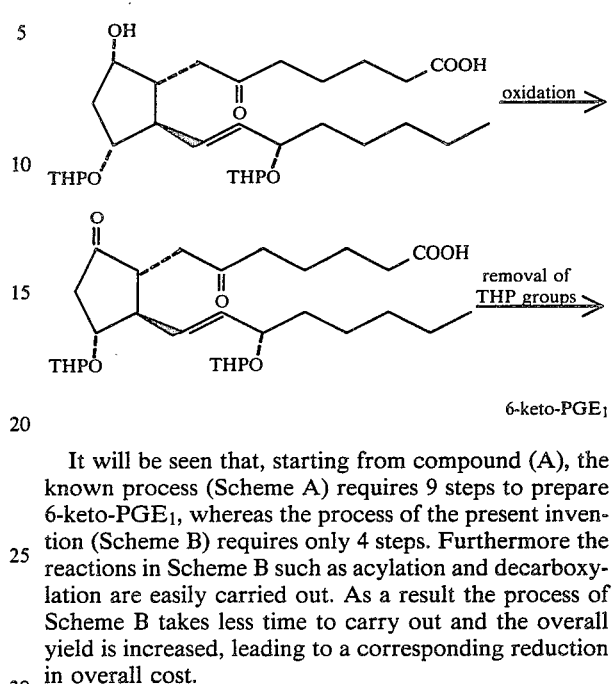

6-keto-PGE$_1$

It will be seen that, starting from compound (A), the known process (Scheme A) requires 9 steps to prepare 6-keto-PGE$_1$, whereas the process of the present invention (Scheme B) requires only 4 steps. Furthermore the reactions in Scheme B such as acylation and decarboxylation are easily carried out. As a result the process of Scheme B takes less time to carry out and the overall yield is increased, leading to a corresponding reduction in overall cost.

The present invention provides compounds of the general formula:

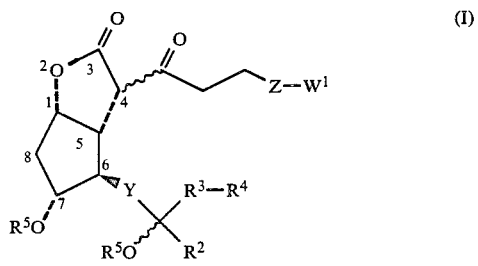

(I)

wherein Y and Z, which may be the same or different, each represents a trans-vinylene group (i.e.

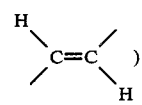

)

or an ethylene group (i.e. —CH$_2$—CH$_2$—), R$^2$ represents a hydrogen atom or a methyl or ethyl group, R$^3$ represents a single bond or an alkylene group of 1 to 5 carbon atoms, R$^4$ represents an alkyl group of 1 to 8 carbon atoms, a cycloalkyl group of 4 to 7 carbon atoms unsubstituted or substituted by at least one alkyl group of 1 to 8 carbon atoms or a phenyl or phenoxy group unsubstituted or substituted by at least one halogen atom, trifluoromethyl group or alkyl group of 1 to 4 carbon atoms, R$^5$ represents a hydroxy-protecting group which can be removed in acidic conditions and W$^1$ represents a group of the formula: —COOR$^1$, —CON(R$^6$), —CH$_2$OR$^5$ or —CH(OR$^7$)CH$_2$OR$^5$ (in which R$^1$ represents a hydrogen atom or an alkyl group of 1 to 12 carbon atoms, the groups R$^6$, which may be the same or different, each represents an alkyl group of 1 to 4 carbon atoms, a phenyl group or an aralkyl group of 7 to 12 carbon atoms or $R^7$ represents an acyl group of 2 to 12 carbon atoms and $R^5$ is as hereinbefore defined) with the proviso that, when $R^3$ represents a single bond, $R^4$ does not represent a substituted or unsubstituted phenoxy group.

It is to be understood that alkyl and alkylene groups within the definitions of various symbols in this specification and the accompanying claims may be straight or branched-chain.

In the above structural formulae and in other structural formulae in this specification, the broken line (---) indicates the α-configuration, the bold line (—) indicates the β-configuration, the wavy line (∼) indicates the α-configuration or the β-configuration or a mixture thereof.

Examples of alkylene groups of 1 to 5 carbon atoms represented by $R^3$ are methylene, ethylene, trimethylene, tetramethylene and pentamethylene groups and isomers thereof.

Examples of the alkyl groups of 1 to 8 carbon atoms represented by $R^4$ are methyl, ethyl, propyl, butyl, pentyl, hexyl, heptyl and octyl groups and isomers thereof.

Examples of the cycloalkyl groups of 4 to 7 carbon atoms unsubstituted or substituted by at least one alkyl group of 1 to 8 carbon atoms represented by $R^4$ are cyclobutyl, cyclopentyl, cyclohexyl and cycloheptyl groups and such groups in which one or more hydrogen atoms are replaced by alkyl groups of 1 to 8 carbon atoms named above, as examples of alkyl groups represented by $R^4$.

Examples of the halogen atom substituent on the phenyl or phenoxy group represented by $R^4$ are fluorine, chlorine, bromine and iodine atoms and examples of the alkyl group of 1 to 4 carbon atoms as substituents are methyl, ethyl, propyl and butyl groups and isomers thereof. Preferred groupings —$R^3$—$R^4$ are, for example, n-pentyl, 1-methylpentyl, 2-methylpentyl, 3-methylpentyl, 4-methylpentyl, 1,1-dimethylpentyl, 1,2-dimethylpentyl, 1,4-dimethylpentyl, 1-ethylpentyl, 2-ethylpentyl, 1-propylpentyl, 2-propylpentyl, n-hexyl, 1-methylhexyl, 2-methylhexyl, 1,1-dimethylhexyl, 1-ethylhexyl, 2-ethylhexyl, n-heptyl, 2-ethylheptyl, n-nonyl, n-undecyl, cyclobutyl, (1-propyl)cyclobutyl, (1-butyl)cyclobutyl, (1-pentyl)cyclobutyl, (2-propyl)cyclobutyl, (3-ethyl)cyclobutyl, (3-propyl)cyclobutyl, cyclopentyl, 1-cyclopentylethyl, 2-cyclopentylethyl, 2-cyclopentylpropyl, (2-ethyl)cyclopentyl, (2-propyl)cyclopentyl, (2-butyl)cyclopentyl, (1-methyl-3-propyl)cyclopentyl, (3-butyl)cyclopentyl, (2-methyl-3-propyl)cyclopentyl, cyclohexyl, (3-ethyl)cyclohexyl, (4-methyl)cyclohexyl, (4-ethyl)cyclohexyl, (4-propyl)cyclohexyl, (2,6-dimethyl)cyclohexyl, cyclohexylmethyl, (1-methyl)cyclohexylmethyl, 1-cyclohexylethyl, 2-cyclohexylethyl, (1-methyl-1-cyclohexyl)ethyl, 1-cycloheptylethyl, phenyl, benzyl, α-phenylethyl, β-phenylethyl, 1-phenylpentyl, phenoxymethyl, (3-chlorophenoxy)methyl, (4-chlorophenoxy)methyl and (3-trifluoromethylphenoxy)methyl: n-pentyl, 2-methylhexyl, 3-chlorophenoxymethyl and 3-butylcyclopentyl are especially preferred and $R^2$ is preferably hydrogen.

Examples of the hydroxy protecting group which can be removed under acidic conditions are heterocyclic groups such as tetrahydropyran-2-yl, tetrahydrofuran-2-yl and tetrahydrothiopyran-2-yl groups, ether groups such as 1-ethoxyethyl, 1-methoxy-1-methylethyl, 1-methoxycyclohexyl and 1-methoxy-1-phenylethyl, trisubstituted silyl groups such as trimethylsilyl, triethylsilyl, tributylsilyl, tert-butyldimethylsilyl, tribenzylsilyl and triphenylsilyl groups and trityl group; tetrahydropyran-2-yl and 1-ethoxyethyl groups are preferred.

In $W^1$ in general formula (I), examples of the alkyl group of 1 to 12 carbon atoms represented by $R^1$ in the group —$COOR^1$ are methyl, ethyl, propyl, butyl, pentyl, hexyl, heptyl, octyl, nonyl, decyl, undecyl and dodecyl and isomers thereof; examples of the alkyl group of 1 to 4 carbon atoms represented by $R^6$ in the group —$CON(R^6)_2$ are methyl, ethyl, propyl and butyl and isomers thereof and examples of the aralkyl group of 7 to 12 carbon atoms are benzyl, 1-phenylethyl, 2-phenylethyl, 3-phenylbutyl, 4-phenylbutyl, 1-(2-naphthyl)ethyl and 2-(1-naphthyl)ethyl, and examples of the acyl group of 2 to 12 carbon atoms represented by $R^7$ in the group —$CH(OR^7)CH_2OR^5$ are acetyl, chloroacetyl, dichloroacetyl, trichloroacetyl, trifluoroacetyl, propionyl, butyryl, isobutyryl, valeryl, benzoyl and naphthyloyl. The groups $COOR^1$ and $CH(OR^7)CH_2OR^5$ are preferred.

Preferably $R^1$ represents a hydrogen atom or an alkyl group of 1 to 4 carbon atoms, e.g. methyl; $R^6$ preferably represents an alkyl group of 1 to 4 carbon atoms, e.g. methyl; preferably $R^7$ represents acetyl.

The preferred configuration of the $OR^5$ group in the side chain is the α-configuration.

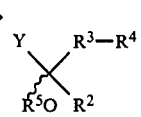

The symbol Y preferably represents trans-vinylene.

The present invention is concerned with all compounds of general formula (I) in the optically active "natural" form or its enantiomeric form or mixtures thereof, more particularly the racemic form consisting of an equimolecular mixture of the "natural" form and its enantiomeric form.

The compounds of general formula (I) have at least six asymmetric centres, i.e. the carbon atoms at the 1-, 4-, 5-, 6- and 7-positions and the carbon atom attached to the $OR^5$ group in the side chain attached to the 6-position. When an alkyl group or an alkylene group represented by various substituents is branched-chain or when a cycloalkyl group represented by $R^4$ is a substituted cycloalkyl group, other asymmetric centres may occur. The existence of assymmetric centres gives rise to isomerism. In the compounds of general formula (I), the substituents attached to the carbon atoms at the 1-, 5- and 7-positions of the bicyclic skeleton (the cyclopentane ring made up of the carbon atoms at the 1-, 5-, 6-, 7- and 8-positions forms the foundation) are cis- to each other and the substituent attached to the carbon atom at the 6-position is trans-to the substituents attached to the carbon atoms at the 1-, 5- and 7-positions. It is to be understood that all isomers and mixtures thereof as mentioned above are to be considered within the scope of general formula (I).

According to a feature of the present invention, compounds of the general formula (I) are prepared by acylation at the 4-position of a compound of the general formula:

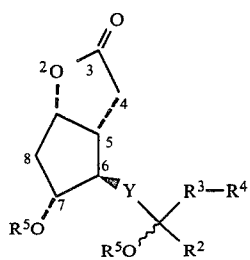

(II)

(wherein all of the symbols are as hereinbefore defined) with a reactive derivative of a carboxylic acid of the general formula:

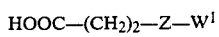

(wherein all of the symbols are as hereinbefore defined) to introduce the side chain $-CO(CH_2)_2-Z-W^1$. The selective acylation at the 4-position of compounds of the general formula (II) may be carried out by reacting a compound of the general formula (II) with a lithium compound for example compound of the general formula:

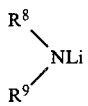

(wherein $R^8$ and $R^9$, which may be the same or different, each represents an alkyl group of 1 to 6 carbon atoms or a cycloalkyl group of 3 to 6 carbon atoms), or an alkali metal alkoxide such as sodium tert-butoxide or potassium tert-butoxide, or an alkali metal bis(trialkylsilyl)amide such as sodium bis(trimethylsilyl)amide, preferably lithium diisopropylamide (LDA), in an inert organic solvent such as toluene, tetrahydrofuran, hexane, pentane or diethyl ether, preferably in toluene, at a temperature from −78° C. to room temperature, preferably from −78° C. to −30° C.; the reaction with the reactive derivative is also carried out at a temperature from −78° C. to room temperature. Examples of the reactive acidic derivatives are the acid halide (preferably an acid chloride), acid anhydride (an internal acid anhydride is included when $W^1$ represents the formula −COOH, e.g.

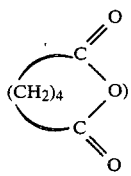

or a diester compound (in which $W^1$ represents −COOR$^1$ and $R^1$ is other than hydrogen), or a mixed acid anhydride with, for example, tert-butylchloroformate.

The starting materials of general formula (II) may be prepared by the methods described in the following literature references and patent specifications, or obvious modifications thereof:

(A) when $R^3$-$R^4$ represents a straight or branched chain alkyl group, by the method described in U.S. Pat. No. 4,061,865, British Patent No. 1398291 and Japanese Patent Publication Nos. 49-124048 and 50-101340; when $R^3$-$R^4$ represents an n-pentyl group, they are obtained by the method described in J. Am. Chem. Soc., 92 397 (1970);

(B) when $R^3$ represents a single bond or a straight or branched chain alkylene group and $R^4$ represents a substituted or unsubstituted cycloalkyl group, they are obtained by the method described in U.S. Pat. Nos. 3,966,792, 4,045,468, 4,061,865 and 4,117,119 and Japanese Patent Publication Nos. 50-148339 and 53-25544;

(C) when $R^3$ represents a single bond or a straight or branched chain alkylene group and $R^4$ represents a substituted or unsubstituted phenyl group, they are obtained by the method described in U.S. Pat. No. 4,061,865;

(D) when $R^3$ represents a straight or branched chain alkylene group and $R^4$ represents a substituted or unsubstituted phenoxy group, they are obtained by the method described in U.S. Pat. No. 4,065,632 and Japanese Patent No. 1214209

The reactive carboxylic acid derivatives used in the acylation reaction can be purchased or can be prepared by known methods.

According to a feature of the present invention the intermediates of general formula (I) of the present invention may be converted into the 6-keto-PGs of the general formula (III) hereinafter described by the series of reactions depicted schematically below in Scheme C.

The configuration of the asymmetric carbon at the 4-position of the bicyclic compound of general formula (I) is R-configuration, S-configuration or a mixture thereof, but the asymmetric carbon disappears by decarboxylation in the step [a] and therefore the final products are not related to the asymmetric carbon atom at the 4-position.

The hydroxy-protecting groups $R^5$ in the compounds of the present invention, which are removed by hydrolysis in step [c] of Scheme C, are groups which can be removed under acidic conditions without affecting other parts of the molecule.

Scheme C

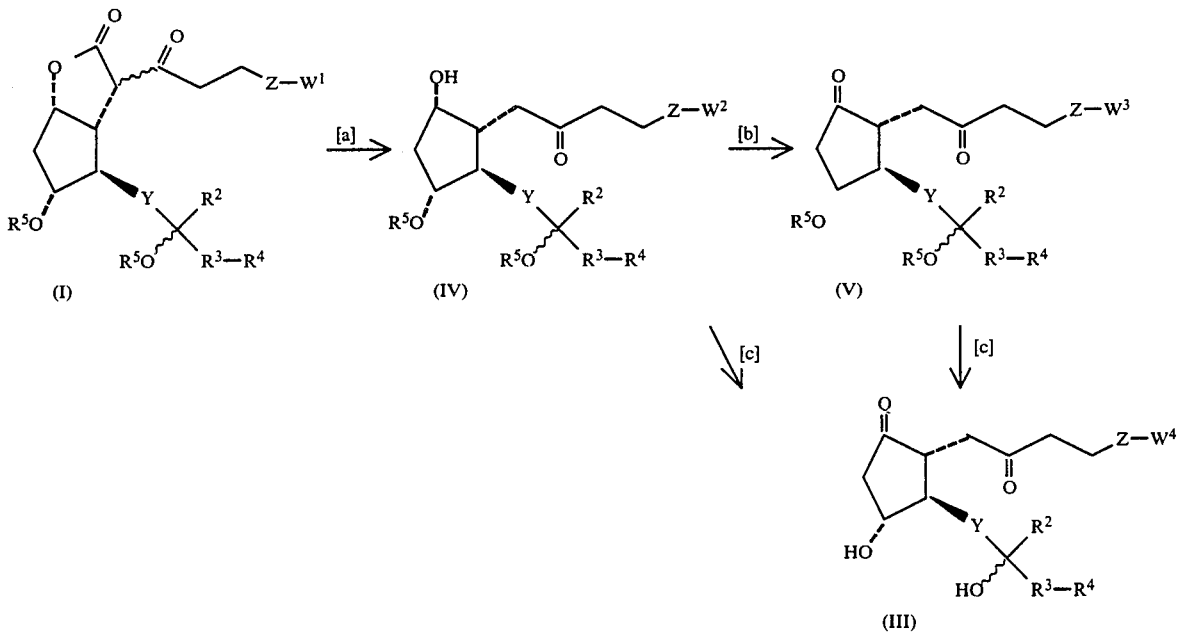

wherein W² represents a group of the formula: —COOR¹, —CH₂OR², —CON(R⁶) or —CH(OH)CH₂OR⁵ (wherein the various symbols are as hereinbefore defined), W³ represents a group of the formula: —COOR¹, —CH₂OR⁵, —CON(R⁶)₂ or —COCH₂OR⁵(wherein the various symbols are as hereinbefore defined), W⁴ represents a group of the formula: —COOR¹, —CH₂OH, —CON(R⁶) or —COCH₂OH (wherein the various symbols are as hereinbefore defined), Q represents a group of the formula

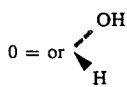

and the other symbols are as hereinbefore defined, with the proviso that W⁴ does not represent a group of the formula —COCH₂OH when Q represents a group of the formula

All of the reaction steps in Scheme C may be conducted by known methods.

For example, the decarboxylation step (a) may be carried out using a base such as potassium hydroxide or sodium hydroxide in a mixture of a lower alkanol such as methanol or ethanol and water, at a temperature from room temperature to the reflux temperature of the reaction mixture. When W¹ represents an ester group COOR¹ in which R¹ is other than hydrogen, the ester is saponified to a free carboxylic acid by this reaction. The free carboxylic acid may be esterified by known methods, if desired, for example, by diazomethane, if a methyl ester is desired, because of the easy purification.

The oxidation step (b) may be carried out by using, for example;

(1) dimethylsulfide-N-chlorosuccinimide complex, thioanisole-N-chlorosuccinimide complex, dimethylsulfide-chlorine complex or thioanisole-chlorine complex in a halogenated hydrocarbon such as chloroform, methylene chloride or carbon tetrachloride or in toluene at a temperature from 0° C. to −30° C. followed by treatment with triethylamine (cf. J. Amer, Chem. Soc., 94, 7586 (1972)).

(2) using chromium trioxide-pyridine complex (e.g. Collins reagent) in a halogenated hydrocarbon such as chloroform, methylene chloride or carbon tetrachloride at a temperature from room temperature to 0° C., preferably at 0° C., (3) using Jones reagent below room temperature, or (4) using oxalyl chloride and dimethylsulfoxide in a halogenated hydrocarbon such as chloroform or methylene chloride at a temperature from −50° C. to −60° C. (Swern oxidation), and then treatment with triethylamine.

The step (c) to remove protecting groups, may be carried out, for example:

(1) in an aqueous solution of an organic acid such as acetic acid, propionic acid, oxalic acid or p-toluenesulfonic acid or an aqueous solution of an inorganic acid such as hydrochloric acid or sulfuric acid at a temperature from room temperature to 75° C. (preferably below 45° C.), suitably in the presence of a water-miscible organic solvent, for example a lower alkanol such as methanol or ethanol (preferably methanol) or an ether such as 1,2-dimethoxyethane, dioxan or tetrahydrofuran (preferably tetrahydrofuran).

(2) by mild hydrolysis in the presence of an organic acid such as p-toluenesulfonic acid or trifluoroacetic acid in an anhydrous alkanol such as methanol or ethanol at a temperature from 10° C. to 45° C.

The hydrolysis is preferably carried out using a mixture of hydrochloric acid, water and tetrahydrofuran, a mixture of hydrochloric acid, water and methanol, a mixture of acetic acid, water and tetrahydrofuran or a mixture of p-toluenesulfonic acid and anhydrous methanol.

In the reactions hereinbefore described to convert intermediates of general formula (I) to 6-keto-PGs, the group $W^1$ is converted to a group $W^4$, via groups $W^2$ and $W^3$.

The conversions for each of the groups represented by $W^1$, $W^2$, $W^3$ and $W^4$ are shown in the following Table.

| $W^1$ Step (a) → | $W^2$ Step (b) → | $W^3$ Step (c) → | $W^4$ |
|---|---|---|---|
| $COOR^1$ | $COOR^1$ | $COOR^1$ | $COOR^1$ |
| $CH_2OR^5$ | $CH_2OR^5$ | $CH_2OR^5$ | $CH_2OH$ |
| $CON(R^6)_2$ | $CON(R^6)_2$ | $CON(R^6)_2$ | $CON(R^6)_2$ |
| $OR^7$ | $OH$ | $O$ | $O$ |
| \| | \| | \|\| | \|\| |
| $CHCH_2OR^5$ | $CHCH_2OR^5$ | $CCH_2OR^5$ | $CCH_2OH$ |

The following Reference Examples and Examples illustrate the preparation and use of compounds of the present invention. In the Reference Examples and Examples, 'TLC', 'NMR', 'IR', and 'Mass' represent 'Thin layer chromatography', 'Nuclear magnetic resonance spectrum', 'Infrared absorption spectrum' and 'Mass spectrum', respectively. The solvents in parentheses specified in chromatographic separations show the eluents or the developing solvents used. Except when specified otherwise, infrared absorption spectra were recorded by the liquid film method and nuclear magnetic resonance spectra were recorded in deuterochloroform ($CDCl_3$) solution.

The starting materials may be prepared by the Wittig reaction of a known compound, i.e. 2-oxa-6-syn-formyl-7-anti-(tetrahydropyran-2-yloxy)-cis-bicyclo-|3,3,0|octan-3-one:

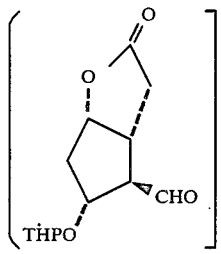

to introduce each ω-chain. The reaction is hereinbefore described in published applications from (A) to (D) and therefore only the physical characteristics of each starting material are shown in the Examples below.

EXAMPLE 1

(E)-2-oxa-4RS-(5-methoxycarbonylvaleryl)-6-syn-|3α-(tetrahydropyran-2-yloxy)oct-1-enyl|-7-anti-(tetrahydropyran-2-yloxy)-cis-bicyclo|3.3.0|octan-3-one Under an atmosphere of argon 3.4 ml of diisopropylamine was added to 30 ml of dry toluene, the mixture was cooled to 0° C. and with stirring 14.5 ml of n-butyllithium was added thereto. After the mixture was stirred for 30 minutes at 0° C., it was then cooled to −78° C. and 5.00 g of (E)-2-oxa-6-syn-[3α-(tetrahydropyran-2-yloxy)-oct-1-enyl]-7-anti-(tetrahydropyran-2-yloxy)-cis-bicyclo[3.3.0]octan-3-one (starting material) in 70 ml of dry toluene was added dropwise thereto during about 30 minutes. The mixture was stirred for 30 minutes at −78° C. and then 2.15 g of 5-methoxycarbonylvaleryl chloride [$CH_3OCO(CH_2)_4COCl$] in 10 ml of dry toluene was added thereto. After the reaction mixture obtained was stirred for 1 hour at −78° C., a mixture of water:tetrahydrofuran (0.5 ml:5 ml) was added thereto and the mixture was warmed to room temperature and then concentrated under reduced pressure to give 6.5 g of the title diketone derivative having the following physical characteristics:

TLC (ethyl acetate:n-hexane=2:1): Rf=0.41;
NMR: δ=5.6–5.2 (2H, m), 5.0 (1H, m), 4.62 (2H, bs), 4.2–3.2 (6H, m), 3.65 (1H, d), 3.64 (3H, s), 0.87 (3H, bt);
IR: ν=1765, 1740, 1720, 1640 cm$^{-1}$;
MS:m/e=494, 476, 463, 445, 374, 348.

Starting material: (E)-2-oxa-6-syn-[3α-(tetrahydropyran-2-yloxy)oct-1-enyl]-7-anti-(tetrahydropyran-2-yloxy)-cis-bicyclo[3.3.0]octan-3-one
TLC (ethyl acetate:n-hexane=1:2): Rf=0.38;
NMR: δ=5.6–5.3 (2H, m), 5.1–4.8 (1H, m), 4.8–4.5 (2H, m), 4.2–3.2 (6H, m), 2.8–2.0 (6H, m), 2.0–1.0 (20H, m), 0.88 (3H, t);
IR: ν=2930, 2870, 1775 cm$^{-1}$.

By the same procedure as described in Example 1, the following compounds (a), (b), (c), (d) and (e) were obtained.

EXAMPLE 1 (a)

(E)-2-oxa-4RS-(5-methoxycarbonylvaleryl)-6-syn-[3α-tetrahydropyran-2-yloxy)-5α-methylnon-1-enyl]-7-anti-(tetrahydropyran-2-yloxy)-cis-bicyclo[3.3.0]octan-3-one
TLC (ethyl acetate:n-hexane=1:2): Rf=0.47;
NMR: δ=5.6–5.2 (2H, m), 5.0 (1H, m), 4.62 (2H, bs), 4.2–3.2 (6H, m), 3.65 (1H, d), 3.64 (3H, s), 0.88 (6H, m);
IR: ν=1765, 1740, 1720, 1640 cm$^{-1}$; MS:m/e=522, 504, 491, 420.

Starting material: (E)-2-oxa-6-syn-[3α-(tetrahydropyran-2-yloxy)-5α-methylnon-1-enyl]-7-anti-(tetrahydropyran-2-yloxy)-cis-bicyclo[3.3.0]octan-3-one
TLC (ethyl acetate:n-hexane=1:2): Rf=0.37;
NMR: δ=5.6–5.1 (2H, m), 5.1–4.8 (1H, m), 4.8–4.6 (2H, m), 4.3–4.0 (2H, m), 4.0–3.7 (2H, m), 3.7–3.3 (2H, m), 2.9–2.4 (3H, m), 2.4–2.0 (3H, m), 2.0–1.0 (21H, m), 1.0–0.8 (6H, m);
IR: ν=2930, 1775 cm$^{-1}$;
MS:m/e=380, 363, 362, 278.

EXAMPLE 1 (b)

(E,E)-2-oxa-4RS-(5-methoxycarbonylpent-4-enoyl)-6-syn-[3α-(tetrahydropyran-2-yloxy)-5α-methylnon-1-enyl]-7-anti-(tetrahydropyran-2-yloxy)-cis-bicyclo[3.3.0]octan-3-one
TLC (ethyl acetate:cyclohexane=1:1): Rf=0.54;
NMR: δ=6.94 (1H, m), 5.86 (1H, bd), 5.4–5.65 (1H, m), 5.3 (1H, m), 5.0 (1H, m), 4.7–6.55 (2H, m), 3.62 (3H, s), 0.89 (6H, m);
IR: ν=1762, 1118, 1658, 973 cm$^{-1}$;
MS:m/e=520, 502, 489, 471, 436, 418, 400, 374.

Starting material: the same compound as used in Example 1 (a)

EXAMPLE 1 (c)

(E)-2-oxa-4RS-(5-methoxycarbonylvaleryl)-6-syn-[3α-(tetrahydropyran-2-yloxy)-4-(3-chlorophenoxy)-but-1-enyl]-7-anti-(tetrahydropyran-2-yloxy)-cis-bicyclo[3.3.0]octan-3-one NMR: δ=7.3–6.5 (4H, m), 5.6–5.2 (2H, m), 5.0 (1H, m), 4.6 (4H, m), 4.2–3.2 (6H, m), 3.65 (1H, d), 3.64 (3H, m);

IR: ν=1770, 1740, 1720, 1640, 1595, 1580 cm$^{-1}$;

MS:m/e=566, 564, 548, 546, 535, 533.

Starting material: (E)-2-oxa-6-syn-[3α-(tetrahydropyran-2-yloxy)-4-(3-chlorophenoxy)but-1-enyl]-7-anti-(tetrahydropyran-2-yloxy)-cis-bicyclo[3.3.0]octan-3-one NMR: δ=7.3–6.6 (4H, m), 5.60 (2H, m), 4.90 (1H, m), 4.65 (2H, m), 4.5–3.3 (6H, m);

IR: ν=1775, 1595, 1580 cm$^{-1}$;

MS:m/e=508, 506, 424, 222.

EXAMPLE 1 (d)

(E)-2-oxa-4RS-(5-methoxycarbonylvaleryl)-6-syn-[3α-(terrahydropyran-2-yloxy)-4S,6S-ethanodec-1-enyl]-7-anti-(tetrahydropyran-2-yloxy)-cis-bicyclo[3.3.0]octan-3-one NMR: δ=5.6–5.2 (2H, m), 4.95 (1H, m), 4.62 (2H, bs), 4.2–3.2 (6H, m), 3.65 (4H, s), 0.88 (3H, bt);

IR: ν=1770, 1740, 1720, 1640 cm$^{-1}$;

MS:m/e=548, 530, 517.

Starting material: (E)-2-oxa-6-syn-[3α-(tetrahydropyran-2-yloxy)-4S,6S-ethanodec-1-enyl]-7-anti-(tetrahydropyran-2-yloxy)-cis-bicyclo[3.3.0]octan-3-one TLC (ethyl acetate:n-hexane=1:3): Rf=0.29;

NMR: δ=4.65 (2H, m), 4.06 (1H, m), 4.0–3.68 (3H, m), 3.58–3.22 (2H, m), 3.5 (2H, m), 2.95 (1H, m), 0.88 (3H, t);

IR: ν=2940, 2850, 1775, 1460, 1440, 1435, 1380, 1350, 1320, 1310, 1260, 1200, 1180, 1160, 1130, 1075, 1030, 1020, 975 cm$^{-1}$;

MS:m/e=406, 388, 365, 304, 286, 281, 229, 197, 174, 123.

EXAMPLE 1 (e)

(E)-2-oxa-4RS-[6RS-acetoxy-6-(2,4-dioxa-3-methylhexyl)-hexanoyl]-6-syn-[3α-(tetrahydropyran-2-yloxy)-4S,6S-ethanodec-1-enyl]-7-anti-(tetrahydropyran-2-yloxy)-cis-bicyclo[3.3.0]octan-3-one NMR: δ=5.6–5.2 (2H, m), 5.00 (1H, m), 4.6 (4H, m), 4.2–3.2 (12H, m), 2.10 (3H, s), 1.32 (3H, d), 1.21 (3H, d), 0.88 (3H, bt);

IR: ν=1765, 1740, 1720, 1640 cm$^{-1}$;

MS:m/e=644, 584, 500.

Starting material: the same compound as used in Example 1 (d)

EXAMPLE 2

(E)-2-oxa-4RS-6-(tetrahydropyran-2-yloxy)-hexanoyl]-6-syn-[3α-(tetrahydropyran-2-yloxy)-4S,6S-ethanodec-1-enyl]-7-anti-(tetrahydropyran-2-yloxy)-cis-bicyclo[3.3.0]octan-3-one Under an atmosphere of argon, 14.5 ml of n-butyl lithium was added to a mixture of 0.34 ml of diisopropylamine and 5 ml of dry toluene at 0° C. with stirring. The mixture was cooled to −78° C. and 490 mg of (E)-2-oxa-6-syn3α-(tetrahydropyran-2-yloxy)-4S,6S-ethanodec-1-enyl]-7-anti-(tetrahydropyran-2-yloxy)-cis-bicyclo[3.3.0]-octan-3-one (starting material) in 5 ml of dry toluene was added thereto. After the mixture was stirred for 30 minutes at the same temperature, 276 mg of 6-(tetrahydropyran-2-yloxy)caproic acid methyl ester in 3 ml of dry toluene was added thereto. The mixture was then stirred for 1 hour at the same temperature and then warmed to room temperature. After 1 hour water was added to the reaction mixture and the mixture was then neutralized with oxalic acid and extracted with ethyl acetate. The extract was washed with water and a saturated aqueous solution of sodium chloride and dried and concentrated under reduced pressure. The residue was purified by column chromatography on silica gel (n-hexane:ethyl acetate=2:1) to give 380 mg of the title compound having the following physical characteristics:

TLC (n-hexane:ethyl acetate=2:1): Rf:=0.41;

NMR: δ=5.6–5.2 (2H, m), 5.00 (1H, m), 4.62 (3H, m), 3.60(1H, d, J=3 Hz);

IR: ν=1770, 1745, 1650 cm$^{-1}$;

MS:m/e=586, 502.

Starting material: the same compound as used in Example 1 (d)

REFERENCE EXAMPLE 1

(13E)-(9α,11α,15S)-6-oxo-9-hydroxy-11,15-bis(tetrahydropyran-2-yloxy)prost-13-enoic acid 100 ml of a mixture of water and methanol (1:1) and 10 ml of 5 M aqueous solution of potassium hydroxide were added to 6.5 g of the diketone derivative prepared in Example 1 and the mixture was refluxed for 2 hours. After cooling to room temperature, an aqueous solution of oxalyl chloride was added to the reaction mixture and after the mixture was adjusted to pH 5, it was extracted with ethyl acetate and the extract was concentrated under reduced pressure to give 6.8 g of the title compound having the following physical characteristic:

TLC (ethyl acetate): Rf=0.36.

By the same procedure as described in Reference Example 1, the following compounds (a), (b), (d), (e) and (f) were obtained.

REFERENCE EXAMPLE 1 (a)

(13E)-(9α,11α,15S,17S)-6-oxo-9-hydroxy-11,15-bis(-tetrahydropyran-2-yloxy)-17,20-dimethylprost-13-enoic acid TLC (ethyl acetate): Rf=0.33.

Starting material: (E)-2-oxa-4RS-(5-methoxycarbonylvaleryl)-6-syn-[3α-(tetrahydropyran-2-yloxy)-5α-methylnon-1-enyl]-7-anti-(tetrahydropyran-2-yloxy)-cis-bicyclo[3.3.0]octan-3-one (prepared in Example 1 (a))

REFERENCE EXAMPLE 1 (b)

(2E, 13E)-(9α,11α,15S,17S)-6-oxo-9-hydroxy-11,15-bis(tetrahydropyran-2-yloxy)-17,20-dimethylprost-2,13-dienoic acid TLC (ethyl acetate): Rf=0.20.

Starting material: (E,E)-2-oxa-4RS-(5-methoxycarbonylpent-4-enoyl)-6-syn-[3α-(tetrahydropyran-2-yloxy)-5α-methylnon-1-enyl]-7-anti-(terrahydropyran-2-yloxy)-cis-bicyclo[3.3.0]octan-3-one (prepared in Example 1 (b))

REFERENCE EXAMPLE 1 (d)

(13E)-(9α,11α,15S,16S,18S)-6-oxo-9-hydroxy-11,15-bis(tetrahydropyran-2-yloxy)-16,18-ethano-20-ethylprost-13-enoic acid TLC (ethyl acetate): Rf=0.21.

Starting material: (E)-2-oxa-4RS-(5-methoxycarbonylvaleryl)-6-syn-[3α-(tetrahydropyran-2-yloxy)-4S,6S-ethanodec-1-enyl]-7-anti-(tetrahydropyran-2-yloxy)-cis-bicyclo[3.3.0]octan-3-one (prepared in Example 1 (d))

REFERENCE EXAMPLE 1 (e)

(13E)-(1RS,9α,11α,15S,16S,18S)-1-(2,4-dioxa-3-(methylhexyl)-1,9-dihydroxy-6-oxo-11,15-bis(tetrahydropyran-2-yloxy)-16,18-ethano-20-ethylprost-13-ene TLC (ethyl acetate:cyclohexane=1:1): Rf=0.09;
NMR: δ=5.5 (1H, m), 5.3 (1H, m), 4.7–4.4 (6H, m), 4.1–3.2 (12H, m), 1.18 (3H, t), 0.87 (3H, m);
IR: ν=3470, 1710, 1132, 1018, 976 cm$^{-1}$.

Starting material: (E)-2-oxa-4RS-[6RS-acetoxy-6-(2,4-dioxa-3-methylhexyl)-hexanoyl]-6-syn-[3α-(tetrahydropyran-2-yloxy)-4S,6S-ethanodec-1-enyl]-7-anti-(tetrahydropyran-2-yloxy)-cis-bicyclo[3,3,0]-octan-3-one (prepared in Example 1 (e))

REFERENCE EXAMPLE 1 (f)

(13E)-(11α, 15S,16S,18S)-1,11,15-tris(tetrahydropyran-2-yloxy)-6-oxo-9α-hydroxy-16,18-ethano-20-ethylprost-13-ene TLC (cyclohexane:ethyl acetate=1:1): Rf=0.38;
NMR: δ=5.7–5.2 (2H, m), 4.8–4.5 (3H, m), 0.89 (3H, m);
IR: ν=3450, 1710 (weak), 1020, 985 cm$^{-1}$;
MS:m/e=644, 558, 545, 475, 459, 440.

Starting material: (E)-2-oxa-4RS-[6-(tetrahydropyran-2-yloxy)hexanoyl-6-syn-[3α-(tetrahydropyran-2-yloxy)-4S,6S-ethanodec-1-enyl]-7-anti-(tetrahydropyran-2-yloxy)-cis-bicyclo[3.3.0]octan-3-one (prepared in Example 2)

REFERENCE EXAMPLE 1 (c)

(13E)-(9α, 11α,15S)-6-oxo-9-hydroxy-11,15-bis (tetrahydropyran-2-yloxy)-16-(3-chlorophenoxy)-17,18,19,20-tetranorprost-13-enoic acid methyl ester TLC (ethyl acetate:cyclohexane=1:2): Rf=0.15;
NMR: δ=7.38–6.70 (4H, m), 5.75–5.46 (2H, m), 3.67&3.66 (3H, each s);
IR: ν=2945, 1740, 1720, 1590, 1580 cm$^{-1}$.

Starting material: (E)-2-oxa-4RS-(5-methoxycarbonylvaleryl)-6-syn-[3α-(tetrahydropyran-2-yloxy)-4-(3-chlorophenoxy)but-1-enyl]-7-anti-(tetrahydropyran-2-yloxy)-cis-bicyclo[3.3.0]octan-3-one (prepared in Example 1 (c)).

The starting material was decarboxylated by the procedure described in Reference Example 1 and the free carboxylic acid obtained was then esterified using diazomethane.

REFERENCE EXAMPLE 2

(13E)-(11α,15S)-6,9-dioxo-11,15-bis(tetrahydropyran-2-yloxy)prost-13-enoic acid 6.8 g of the 6-oxo-9-hydroxy derivative prepared in Reference Example 1 was dissolved in 100 ml of acetone, the mixture was cooled to −25° C. and with stirring 1 ml of Jones reagent was added thereto; after 5, 10, 30, 40 and 60 minutes, 1 ml of Jones reagent was added thereto and the mixture was then stirred for an hour at the same temperature. 3 ml of isopropyl alcohol was added to the reaction mixture, the mixture was warmed to room temperature, 200 ml of water was added thereto and the mixture was extracted with ethyl acetate (200 ml×1 time, 100 ml×2 times).

The extract was dried and concentrated under reduced pressure. The residue was purified by column chromatography on silica gel (ethyl acetate:n-hexane=3:7→4:6) to give 3.00 g of the title compound having the following physical characteristics:

TLC (diethyl ether): Rf=0.36;
NMR: δ=5.7–5.3 (2H, m), 4.8–4.6 (2H, m), 4.3–3.95 (2H, m), 3.95–3.7 (2H, m), 3.6–3.4 (2H, m), 2.9–2.2 (9H, m), 1.9–1.4 (18H, m), 1.4–1.1 (6H, m), 0.86 (3H, t);
MS:m/e=434, 350, 332.

By the same procedure as described in Reference Example 2, the following compounds (a), (b), (c), (d), (e) and (f) were obtained.

REFERENCE EXAMPLE 2 (a)

(13E)-(11α,15S,17S)-6,9-dioxo-11,15-bis(tetrahydropyran-2-yloxy)-17,20-dimethylprost-13-enoic acid TLC (ethyl acetate:n-hexane=1:1): Rf=0.09;
NMR: δ=5.7–5.3 (2H, m), 4.8–4.6 (2H, m), 4.3–4.0 (2H, m), 4.0–3.7 (2H, m), 3.7–3.3 (2H, m), 2.8–2.6 (3H, m), 2.6–2.2 (7H, m), 1.9–1.1 (25H, m), 1.0–0.8 (6H, m);
IR: ν=2930, 1740, 1715 cm$^{-1}$;
MS:m/e=462, 445, 378.

Starting material:
(13E)-(9α,11α,15S,17S)-6-oxo-9-hydroxy-11,15-bis(tetrahydropyran-2-yloxy)-17,20-dimethylprost-13-enoic acid (prepared in Reference Example 1 (a))

REFERENCE EXAMPLE 2 (b)

(2E,13E)-(11α,15S,17S)-6,9-dioxo-11,15-bis(tetrahydropyran-2-yloxy)-17,20-dimethylprosta-2,13-dienoic acid TLC (ethyl acetate): Rf=0.28;
NMR: δ=8.0 (1H, bs), 7.0 (1H, m), 5.8 (1H, d), 5.5 (2H, m), 4.7 (2H, m), 3.7–4.4 (4H, m), 3.3–3.6 (2H, m), 0.9 (6H, m);

Starting material: (2E,13E)-(9α,11α,15S,17S)-6-oxo-9-hydroxy-11,15-bis(tetrahydropyran-2-yloxy)-16-dimethylprost 2,13-dienoic acid (prepared in Reference Example 1 (b))

REFERENCE EXAMPLE 2 (c)

(13E)-(11α,15S)-6,9-dioxo-11,15-bis(tetrahydropyran-2-yloxy)-16-(3-chlorophenoxy)-17,18,19,20-tetranorprost-13-enoic acid methyl ester TLC (ethyl acetate:cyclohexane=1:2): Rf=0.31;
IR: ν=1750, 1720, 1590, 1580 cm$^{-1}$;
NMR: δ=7.30–6.56 (4H, m), 5.83–5.47 (2H, m), 4.90–4.56 (2H, m), 3.58 (3H, s).

Starting material:
(13E)-(9α,11α,15S)-6-oxo-9-hydroxy-11,15-bis(tetrahydropyran-2-yloxy)-16-(3-chlorophenoxy)-17,18,19,20-tetranorprost-13-enoic acid methyl ester (prepared in Reference Example 1 (c))

REFERENCE EXAMPLE 2 (d)

(13E)-(11α,15S,16S,18S)-6.9-dioxo-11,15-bis (tetrahydropyran-2-yloxy)-16,18-ethano-20-ethylprost-13-enoic acid TLC (ethyl acetate): Rf=0.46;
MS:m/e=488, 404, 386, 279.

Starting material:
(13E)-(9α,11α,15S,16S,18S)-6-oxo-9-hydroxy-11,15-bis(tetrahydropyran-2-yloxy)-16,18-ethano-20-ethylprost-13-enoic acid (prepared in Reference Example 1 (d))

REFERENCE EXAMPLE 2 (e)

(13E)-(11α,15S,16S,18S)-1-(2,4-dioxa-3-methylhexyl)-1,6,9-trioxo-11,15-bis-(tetrahydropyran-2-yloxy)-16,18-ethano-20-ethylprost-13-ene TLC (ethyl acetate:cyclohexane=1:1): Rf=0.36;

NMR: δ=5.6 (1H, m), 5.4 (1H, m), 4.83 (3H, m), 4.78 (1H, q), 4.8–4.6 (2H, m), 4.7–4.4 (4H, m), 4.2–4.0 (1H, m), 4.09 (2H, d), 1.34 (3H, d), 1.19 (3H, t), 0.88 (3H, t);
IR: $\nu$=1743, 1715, 973 cm$^{-1}$;
MS:m/e=575, 546, 529, 472, 444, 426, 421, 418, 400.
Starting Material: (13E)-(1RS-9α,11α,15S,16S,18S)-1-(2,4-dioxa-3-methylhexyl)-1,9-dihydroxy-6-oxo-11,15-bis(tetrahydropyran-2-yloxy)-16,18-ethano-20-ethylprost-13-ene (prepared in Reference Example 1 (e))

REFERENCE EXAMPLE 2 (f)

(13E)-(11α,15S,,16S,18S)-1,11,15-tris(tetrahydropyran-2-yloxy)-6,9dioxo-16,18-ethano-20-ethylprost-13-ene
TLC (cyclohexane:ethyl acetate=2:1): Rf=0.24;
NMR: δ=5.8–5.2 (2H, m), 4.85–4.5 (3H, m), 0.89 (3H, m);
IR: $\nu$=1743, 1710, 1032, 974 cm$^{-1}$;
MS:m/e=558, 474, 456, 390, 372, 354.
Starting material: (13E)-(11α,15S,16S,18S)-1,11,15-tris(tetrahydropyran-2-yloxy)-6-oxo-9α-hydroxy-16,18-ethano-20-ethylprost-13-ene (prepared in Reference Example 1 (f))

REFERENCE EXAMPLE 3

(13E)-(11α,15S)-6,9-dioxo-11,15-dihydroxyprost-13-enoic acid (6-keto-PGE$_1$)

3.0 g of 11,15-bis(tetrahydropyran-2-yloxy) derivative prepared in Reference Example 2 was dissolved in a mixture of 50 ml of acetic acid, water and tetrahydrofuran (65:35:10) and the mixture was stirred for 10 minutes at 80° C. After cooling the reaction mixture with ice, 300 ml of water was added, and the mixture was extracted with ethyl acetate (500 ml×1 time, 150 ml×2 times). The extract was washed with water and a saturated aqueous solution of sodium chloride, dried and concentrated under reduced pressure to give 3.2 g of crude product. The crude product was purified by column chromatography on silica gel (ethyl acetate:n-hexane (1:1)→ethyl acetate→methanol:ethyl acetate (1:5) to give 1.65 g of the title compound having the following physical characteristics:
TLC (1% acetic acid/ethyl acetate): Rf=0.36;
Melting point: 67°–69° C.;
NMR: δ=5.7–5.5 (2H, m), 4.8–4.2 (3H, br), 4.2–4.0 (2H, m), 2.85–2.6 (2H, m), 2.6–2.3 (7H, m), 1.7–1.4 (6H, m), 1.4–1.2 (6H, m), 0.87 (3H, t);
IR(CHCl$_3$): $\nu$=3400, 2940, 1745, 1715 cm$^{-1}$;
MS:m/e=368(M+), 350, 332.
By the same procedure as described in Reference Example 3, the following compounds (a), (b), (c), (d), (e), (f) and (g) were obtained.

REFERENCE EXAMPLE 3 (a)

(13E)-(11α,15S,17S)-6,9-dioxo-11,15-dihydroxy-17,20dimethylprost-13-enoic acid
TLC (1% acetic acid/ethyl acetate): Rf=0.36;
NMR: δ=5.56 (2H, m), 4.2–4.0 (2H, m), 4.3–3.6 (3H, br), 2.9–2.6 (3H, m), 2.6–2.3 (7H, m), 1.7–1.5 (4H, m), 1.5–1.1 (9H, m), 0.9 (6H, m);
IR: $\nu$=3350, 2920, 1735, 1710 cm$^{-1}$;
MS:m/e=378, 360.
Starting material: (13E)-(11α,15S,17S)-6,9-dioxo-11,15-bis(tetrahydropyran-2-yloxy)-17,20-dimethylprost-13-enoic acid (prepared in Reference Example 2 (a))

REFERENCE EXAMPLE 3 (b)

(2E, 13E)-(11α,15S, 17S)-6,9-dioxo-11,15-dihydroxy-17,20-dimethylprost-2,13-dienoic acid
NMR: δ=6.97 (1, dt), 5.80 (1H, d), 5.55 (2H, m), 4.6–3.8 (7H, m), 2.79 (1H, dd), 0.89 (6H, m);
IR: $\nu$=3600–2400, 1740, 1705, 1654, 973 cm$^{-1}$;
MS:m/e=376, 358, 306, 277, 259, 249, 231.
Starting material: (2E,13E)-(11α,15S,17S)-6,9-dioxo-11,15-bis(tetrahydropyran-2-yloxy)-17,20-dimethylprost-2,13-dienoic acid (prepared in Reference Example 2 (b))

REFERENCE EXAMPLE 3 (c)

(13E)-(11α,15S)-6,9-dioxo-11,15-dihydroxy-16-(3-chlorophenoxy)-17,18,19,20-tetranorprost-13-enoic acid methyl ester
TLC (ethyl acetate): Rf=0.42;
NMR: δ=7.31–6.72 (4H, m), 5.82–5.66 (2H, m), 4.60–4.40 (1H, m), 4.30–3.85 (5H, m), 3.65 (3H, s), 2.98–2.15 (10H, m), 1.68–1.45 (4H, m);
IR: $\nu$=2950, 2880, 1740, 1715, 1590, 1580 cm$^{-1}$.
Starting material: (13E)-(11α,15S)-6,9-dioxo-11,15-bis(tetrahydropyran-2-yloxy)-16-(3-chlorophenoxy)-17,18,19,20-tetranorprost-13-enoic acid methyl ester (prepared in Reference Example 2 (c))

REFERENCE EXAMPLE 3 (d)

(13E)-(11α,15S,16S,18S)-6,9-dioxo-11,15-dihydroxy-16,18-ethano-20-ethylprost-13-enoic acid
TLC (ethyl acetate): Rf=0.087;
Melting point: 76°–79° C.;
NMR: δ=5.57 (2H, m), 4.09 (1H, m), 3.83 (1H, m), 2.78 (1H, dd), 0.88 (3H, m);
IR(KBr method): $\nu$=3600–2400, 1747, 1728, 1708, 973 cm$^{-1}$;
MS:m/e=404, 386, 279.
Starting material: (13E)-(11α,15S,16S,18S)-6,9-dioxo-11,15-bis(tetrahydropyran-2-yloxy)-16,18-ethano-20-ethylprost-13-enoic acid (prepared in Reference Example 2 (d))

REFERENCE EXAMPLE 3 (e)

(13E)-(11α,15S,16S,18S)-1-hydroxymethyl-1,6,9-trioxo-11,15-dihydroxy-16,18-ethano-20-erhylprost-13-ene[(16S,18S)-2-decarboxy-2-glycolcyl-16,18-ethano-ω-dihomo-6-keto-PGE$_1$]
TLC (ethyl acetate:formic acid=80:1): Rf=0.21;
Melting point:95°–96° C.;
NMR: δ=5.60 (2H, m), 4.24 (2H, s), 4.12 (1H, m), 3.86 (1H, m), 2.79 (1H, mdd), 0.88 (3H, m);
IR(KBr method): $\nu$=3460, 1748, 1732, 1710, 1288, 970 cm$^{-1}$.
MS:m/e=418, 400, 382, 369, 293, 257, 229.
Starting material: (13E)-(11α,15S,16S,18S)-1-(2,4-dioxa-3-methylhexyl)-1,6,9-trioxo-11,15-bis(tetrahydropyran-2-yloxy)-16,18-ethano-20-ethylprost-13-ene (prepared in Reference Example 2 (e))

REFERENCE EXAMPLE 3 (f)

(13E)-(11α,15S,16S,18S)-1,11,15-trihydroxy-6,9-dioxo-16,18-ethano-20-ethylprost-13-ene-[(16S,18S)-2-decarboxy-2-hydroxymethyl-16,18-ethano-s-dihomo-6-keto-PGE$_1$]
TLC (ethyl acetate:formic acid=400:5): Rf=0.18;
Melting point:92°–95° C.;
NMR: δ=5.6 (2H, m), 4.10 (1H, q), 3.84 (1H, q), 3.64 (2H, t), 2.79 (1H, dd), 2.70 (1H, m), 0.89 (3H, t);

IR(KBr method): ν=3420, 1747, 1710, 975 cm⁻¹;
MS:m/e=390, 372, 364, 265, 247.

Starting material: (13E)-(11α,15S,16S,18S)-1,11,15-tris(tetrahydropyran-2-yloxy)-6,9-dioxo-16,18-ethano-20-ethylprost-13-ene (prepared in Reference Example 2 (f))

REFERENCE EXAMPLE 3 (g)

(13E)-(9α, 11α,15S)-6-oxo-9,11,15-trihydroxyprost-13-enoic acid (6-keto-PGF$_{1α}$)

TLC (1% acetic acid/ethyl acetate): Rf=0.18;
NMR (acetone-d$_6$): δ=5.6-5.4 (2H, m), 4.5 and 4.1 (½H×2, m), 4.0 (1H, m), 3.8 (1H, m), 3.5-2.5 (4H, br), 2.9-2.7 (1H, m), 2.5-1.9 (9H, m), 1.8-1.4 (12H, m), 0.85 (3H, m);
IR(KBr method): ν=3420, 2940, 1700 cm⁻¹.

Starting material: (13E)-(9α,11α,15S)-6-oxo-9-hydroxy-11,15-bis(tetrahydropyran-2-yloxy)-13-enoic acid (prepared in Reference Example 1)

We claim:

1. A compound of the formula:

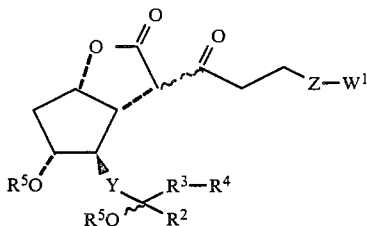
(I)

wherein Y and Z, which may be the same or different, each represents a trans-vinylene group or an ethylene group, R² represents a hydrogen atom or a methyl or ethyl group, R³ represents a single bond or an alkylene group of 1 to 5 carbon atoms, R⁴ represents an alkyl group of 1 to 8 carbon atoms, a cycloalkyl group of 4 to 7 carbon atoms unsubstituted or substituted by at least one alkyl group of 1 to 8 carbon atoms, a phenyl or a phenoxy group unsubstituted or substituted by at least one halogen atom, trifluoromethyl group or alkyl group of 1 to 4 carbon atoms, R⁵ represents a hydroxy-protecting group which can be removed in acidic conditions and W¹ represents a group of the formula: —COOR¹, —CON(R⁶)₂, —CH₂OR⁵ or —CH(OR⁷)CH₂OR⁵ (in which R¹ represents a hydrogen atom or an alkyl group of 1 to 12 carbon atoms, the groups R⁶, which may be the same or different, each represents an alkyl group of 1 to 4 carbon atoms, a phenyl group or an aralkyl group of 7 to 12 carbon atoms, R⁷ represents an acyl group of 2 to 12 carbon atoms and R⁵ is as hereinbefore defined) with the proviso that, when R³ represents a single bond, R⁴ does not represent a substituted or unsubstituted phenoxy group.

2. A compound according to claim 1 wherein W¹ represents a group of the formula: —COOR¹ (in which R¹ represents a hydrogen atom or an alkyl group of 1 to 12 carbon atoms).

3. A compound according to claim 1 wherein W¹ represents a group of the formula: —CH(OR⁷)CH₂OR⁵, in which R⁵ and R⁷ are as defined in claim 1.

4. A compound according to claim 1 wherein R² represents a hydrogen atom and —R³—R⁴ represents n-pentyl, 2-methylhexyl, (3-butyl)cyclopentyl, or (3-chlorophenoxy)methyl.

5. A compound according to claim 1 wherein R⁵ represents a tetrahydropyran-2-yl group or a 1-ethoxyethyl group.

6. A compound according to claim 1 wherein Y represents trans-vinylene.

7. A compound according to claim 1 in which the OR⁵ group in the side chain

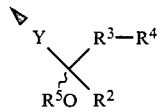

is in α-configuration.

8. A compound according to claim 1 which is:
(E)-2-oxa-4RS-(5-methoxycarbonylvaleryl)-6-syn-[3α-(tetrahydropyran-2-yloxy)oct-1-enyl]-7-anti-(tetrahydropyran-2-yloxy)-cis-bicyclo[3.3.0]octan-3-one,
(E)-2-oxa-4RS-(5-methoxycarbonylvaleryl)-6-syn-[3α-(tetrahydropyran-2-yloxy)-5α-methylnon-1-enyl]-7-anti-(tetrahydropyran-2 yloxy)-cis-bicyclo[3.3.0]octan-3-one,
(E,E)-2-oxa-4RS-(5-methoxycarbonylpent-4-enoyl)-6-syn-[3α-(tetrahydropyran-2-yloxy)-5α-methylnon-1-enyl]-7-anti-(tetrahydropyran-2-yloxy)-cis-bicyclo[3.3.0]octan-3-one,
(E)-2-oxa-4RS-(5-methoxycarbonylvaleryl)-6-syn-[3α-(tetrahydropyran-2-yloxy)-4-(3-chlorophenoxy)but-1-enyl]-7-anti-(tetrahydropyran-2-yloxy)-cis-bicyclo[3.3.0]octan-3-one,
(E)-2-oxa-4RS-(5-methoxycarbonylvaleryl)-6-syn-[3α-(tetrahydropyran-2-yloxy)-4S,6S-ethanodec-1-enyl]-7-anti-(tetrahydropyran-2-yloxy)-cis-bicyclo[3.3.0]octan-3-one,
(E)-2-oxa-4RS-[6RS-acetoxy-6-(2,4-dioxa-3-methylhexyl)-hexanoyl]-6-syn[3-α-(tetrahydropyran-2-yloxy)-4S,6S-ethanodec-1-enyl]-7-anti-(tetrahydropyran-2-yloxy)-cis-bicyclo[3.3.0]octan-3-one, and
(E)-2-oxa-4RS-[6-(tetrahydropyran-2-yloxy)hexanoyl-6-syn-[3α-(tetrahydropyran-2-yloxy)-4S,6S-ethanodec-1-enyl]-7-anti-(tetrahydropyran-2-yloxy)-cis-bicyclo[3.3.0]octan-3-one.

* * * * *